US00PP21187P2

(12) United States Plant Patent
Smith

(10) Patent No.: US PP21,187 P2
(45) Date of Patent: Aug. 10, 2010

(54) ***CHRYSANTHEMUM* PLANT NAMED 'YOMILDRED'**

(50) Latin Name: *Chrysanthemum×morifolium*
Varietal Denomination: Yomildred

(75) Inventor: Mark A. Smith, Fort Myers, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/459,637

(22) Filed: Jul. 6, 2009

(51) Int. Cl.
*A01H 5/00* (2006.01)

(52) U.S. Cl. ..... Plt./288

(58) Field of Classification Search ..... Plt./288
See application file for complete search history.

*Primary Examiner*—June Hwu
(74) *Attorney, Agent, or Firm*—S. Matthew Edwards

(57) ABSTRACT

A new *Chrysanthemum* plant named 'Yomildred,' particularly distinguished by the medium to large, white decorative-type flowers, medium size mounded habit, and a later natural season flowering response.

1 Drawing Sheet

Latin name of the genus and species of the plant claimed: *Chrysanthemum×morifolium.*

Varietal denomination: 'Yomildred'.

BACKGROUND OF THE NEW PLANT

The present invention comprises a new *Chrysanthemum*, botanically known as *Chrysanthemum×morifolium*, and hereinafter referred to by the variety name 'Yomildred'.

'Yomildred' is a product of a planned breeding program. The new cultivar has medium to large, white decorative-type flowers, medium size mounded habit, and a later natural season flowering response.

'Yomildred' originated from a hybridization made in March 2000 in a controlled breeding environment in Salinas, Calif. The seed sowing took place in June 2003 in a controlled environment in Alva, Fla.

The female parent was the unpatented proprietary plant designated '97-LO91' with similar flower type, color and size, a natural season response that is at least 3 days slower, shorter and wider plant habit, and less uniform flowering.

The male parent of 'Yomildred' was an unpatented hybrid seedling identified as '95-L343008' with similar flower color and size, fewer disc florets, a natural season response that is at least 2 days slower, a larger plant size, and flowers less uniformly.

'Yomildred' was selected as one flowering plant within the progeny of the stated cross in November 2003.

The first act of asexual reproduction of 'Yomildred' was accomplished when vegetative cuttings were propagated from the initial selection in December 2003 in a controlled environment in Alva, Fla.

BRIEF SUMMARY OF INVENTION

Horticultural examination of plants grown from cuttings of the plant initiated in December 2003, and continuing thereafter, has demonstrated that the combination of characteristics as herein disclosed for 'Yomildred' are firmly fixed and are retained through successive generations of asexual reproduction.

'Yomildred' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety.

Plant Breeder's Rights for this cultivar have not been applied for. 'Yomildred' has not been made publicly available more than one year prior to the filing of this application.

BRIEF DESCRIPTION OF THE PHOTOGRAPHS

The accompanying photographic drawing shows typical flower and foliage characteristics of 'Yomildred' with colors being as true as possible with an illustration of this type. The photographic drawing shows a flowering potted plant of the new variety, and a close-up of the flowers.

DETAILED BOTANICAL DESCRIPTION

The plant descriptions and measurements were taken in Salinas, Calif. in early June 2009 under natural light. The aforementioned photographs were taken in Gilroy, Calif. in early June 2009 in a greenhouse. These plants were started and grown in six inch pots in Alva, Fla. and were shipped to California in late May 2009.

Plants were grown under conditions which approximate those generally used in commercial potted *Chrysanthemum* production. These plants used in the photograph and descriptions were about 10 weeks old.

Color references are made to The Royal Horticultural Society Colour Chart (R.H.S.) 2001.

TABLE 1

DIFFERENCES BETWEEN THE NEW VARIETY 'YOMILDRED' AND A SIMILAR VARIETY

| | 'Yomildred' | 'Yobrigitte' (U.S. Plant Pat. No. 11,843) |
|---|---|---|
| Flower size: | Little larger | Little smaller |
| Plant habit: | Little taller, rounder | Little shorter, less round |
| Flower lastingness: | Longer lasting | Does not last as long |
| Natural season flower response: | 5 days faster in Northern U.S. | 5 days slower in Northern U.S. |
| Natural season flower response: | 1 week slower in Southern U.S. | 1 week faster in Southern U.S. |

Plant:

*Form, growth and habit.*—Herbaceous decorative garden-type; stems upright and outwardly spreading, freely branching, strong and moderately vigorous growth habit.

*Plant height.*—13-15 cm.
*Plant height (inflorescence included).*—20-22 cm.
*Plant width.*—40-44 cm.
*Garden performance and tolerance to weather.*—Good.
*Crop time to flowering.*—About 50 days.

Roots:
*Number of days to initiate roots.*—4 days at about 21 degrees C.
*Number of days to produce a rooted cutting.*—4 days at 21 degrees C.
*Type.*—Fine, fibrous, free branching.
*Color.*—RHS N155B but whiter.

Foliage:
*Arrangement.*—Alternate, simple.
*Immature, leaf color, upper surface.*—Closest to RHS 137A but more yellow-green.
*Lower surface.*—Closest to RHS 147B.
*Mature, leaf color, upper surface.*—Closest to RHS 137A but more yellow-green.
*Lower surface.*—RHS 147B but slightly lighter.
*Length.*—7.5-8.0 cm.
*Width.*—4.3-4.9 cm.
*Shape.*—Ovate.
*Base shape.*—Attenuate.
*Apex shape.*—Abruptly acute.
*Margin.*—Palmately lobed; slightly serrate.
*Texture, upper surface.*—Bifid T-shaped hairs.
*Lower surface.*—Bifid T-shaped hairs.
*Color of veins, upper surface.*—RHS 147B.
*Color of veins, lower surface.*—RHS 147B.
*Petiole color.*—RHS 147B.
*Length.*—2.8-3.1 cm.
*Diameter.*—0.2 cm.
*Texture.*—Bifid T-shaped hairs.

Stem:
*Quantity of main branches per plant after removal of terminal apex (pinching).*—6-8.
*Quantity of leaves per branch.*—About 14.
*Color of stem.*—RHS 146A but a little more green.
*Length of stem.*—11-14 cm.
*Diameter.*—0.3-0.4 cm.
*Length of internodes.*—0.5-2.0 cm.
*Texture.*—Bifid T-shaped hairs.
*Color of peduncle.*—RHS 146A.
*Length of peduncle.*—0.8-11.0 cm.
*Peduncle diameter.*—0.15 cm.
*Texture.*—Bifid T-shaped hairs.

Inflorescence:
*Type.*—Compositate type, solitary inflorescences (decorative-type) borne terminally above foliage, ray florets arranged acropetally on a capitulum.
*Blooming habit.*—Natural season flowering around mid-October.
*Average quantity of inflorescences per plant.*—About 130.
*Average quantity of inflorescences per lateral stem.*—About 20.
*Lastingness of individual blooms on the plant.*—3½ weeks.
*Fragrance.*—Slightly spicy.

Bud (just before opening/showing color):
*Color.*—Closest to RHS 4C.
*Length.*—0.6-0.8 cm.
*Width.*—0.6-0.9 cm.
*Shape.*—Oblate.

Immature inflorescence:
*Diameter.*—3.5-4.5 cm.
*Color of ray florets, upper surface.*—Closest to RHS 1D.
*Lower surface.*—Closest to RHS 1D.

Mature inflorescence:
*Diameter.*—5.0-6.0 cm.
*Depth.*—About 2.0 cm.
*Total diameter of 'disc'.*—No disc showing.
*Receptacle height.*—0.5 cm.
*Receptacle diameter.*—0.5 cm.

Ray florets:
*Average quantity of florets.*—About 185 in numerous whorls.
*Color of florets, upper surface.*—RHS N155B but whiter with RHS 145B basally.
*Lower surface.*—RHS N155B but whiter with RHS145B basally.
*Length.*—2.2-2.7 cm.
*Width.*—0.5-0.7 cm.
*Shape.*—Oblong to narrowly elliptical.
*Apex shape.*—Praemorse.
*Margin.*—Entire.
*Texture, upper surface.*—Papillose.
*Lower surface.*—Papillose.

Disc florets:
*Average quantity of florets.*—About 5.
*Color of florets.*—RHS 14A.
*Length.*—0.4 cm.
*Width.*—0.1 cm.
*Shape.*—Tubular, enlongated.
*Apex shape.*—Acute, 5 pointed.

Phyllaries:
*Quantity.*—20-24.
*Color, upper surface.*—RHS 146A.
*Lower surface.*—Closest to RHS 189A.
*Length.*—1.0-2.3 cm.
*Width.*—0.2-0.3 cm.
*Shape.*—Lanceolate.
*Apex shape.*—Acute.
*Based.*—Fused.
*Margins.*—Entire; papery and translucent.
*Texture, upper surface.*—Smooth and shiny.
*Lower surface.*—Heavily covered with Bifid T-shaped hairs.

Reproductive organs:
*Gynoecium.*—Found on both florets.
*Pistil quantity.*—1.
*Length.*—0.25 cm.
*Style color.*—RHS 1C.
*Style length.*—0.2 cm.
*Stigma color.*—RHS 1B.
*Stigma shape.*—Biparted.
*Stamens quantity.*—4-5.
*Color of filaments.*—RHS 1C.
*Length filaments.*—0.3 cm.
*Anther color.*—RHS 14B.
*Anther length.*—0.2 cm.
*Anther shape.*—Ligulate.
*Color of pollen.*—RHS 14A.
*Pollen amount.*—Moderate.
*Fertility/seed set.*—Has not been observed on this hybrid.

Disease/pest resistance: Disease resistance or susceptibility has not been observed on this hybrid.

What is claimed is:

1. A new and distinct variety of *Chrysanthemum* plant named 'Yomildred,' substantially as illustrated and described herein.

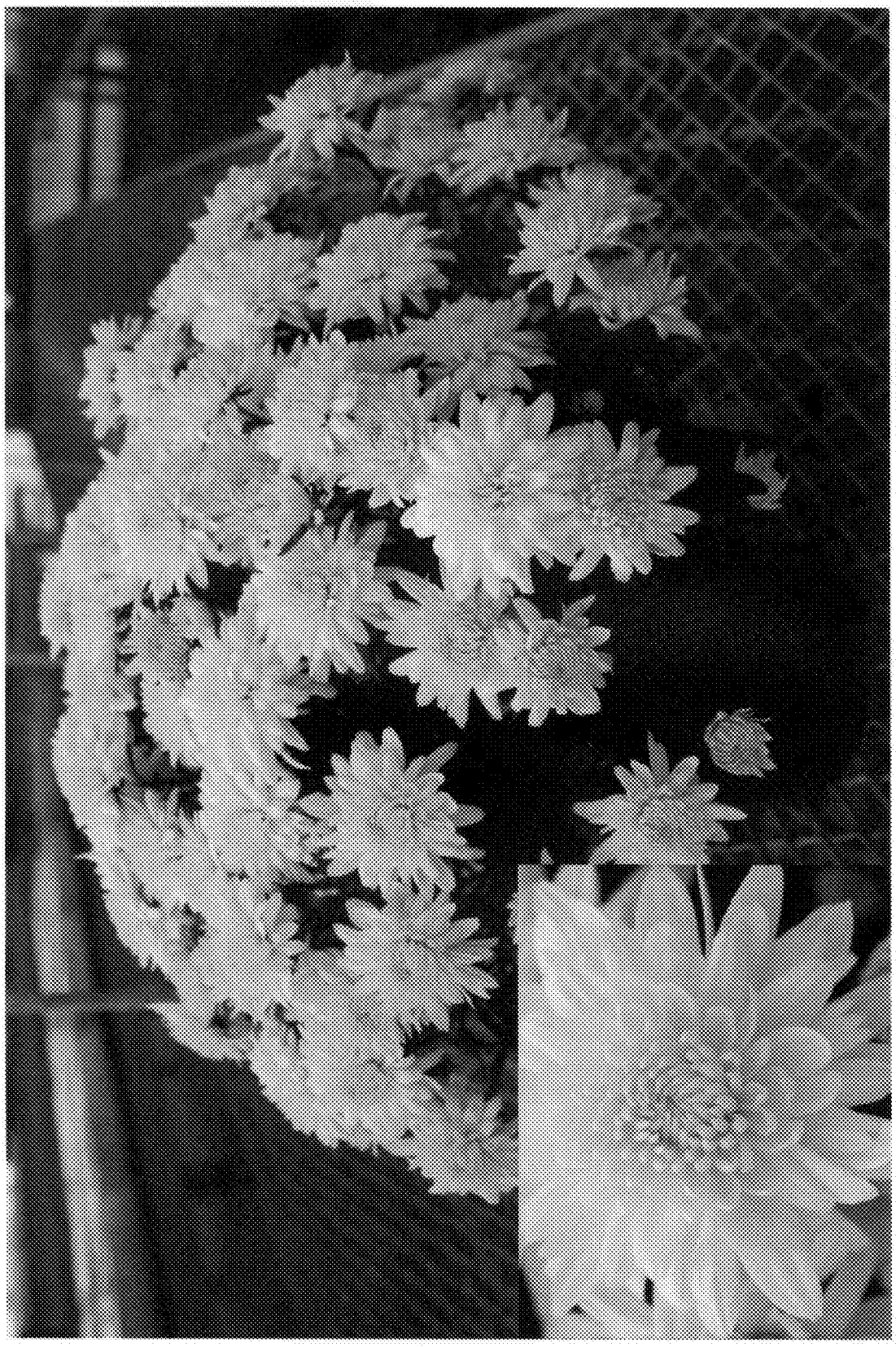

* * * * *